US008843332B2

United States Patent
Sanchez Loureda et al.

(10) Patent No.: US 8,843,332 B2
(45) Date of Patent: Sep. 23, 2014

(54) METHOD AND APPARATUS FOR NOISE REDUCTION AND DATA COMPRESSION

(75) Inventors: Jose Manuel Sanchez Loureda, London (GB); Adam Richard Westbrooke, Kent (GB); Clarke Brunt, London (GB)

(73) Assignee: Onzo Limited, London (GB)

( * ) Notice: Subject to any disclaimer, the term of this patent is extended or adjusted under 35 U.S.C. 154(b) by 299 days.

(21) Appl. No.: 13/061,003

(22) PCT Filed: Nov. 12, 2010

(86) PCT No.: PCT/GB2010/002092
§ 371 (c)(1),
(2), (4) Date: Aug. 24, 2011

(87) PCT Pub. No.: WO2011/058327
PCT Pub. Date: May 19, 2011

(65) Prior Publication Data
US 2011/0301887 A1    Dec. 8, 2011

Related U.S. Application Data

(60) Provisional application No. 61/306,195, filed on Feb. 19, 2010.

(30) Foreign Application Priority Data

| Nov. 12, 2009 | (GB) | 0919785.6 |
| Dec. 18, 2009 | (GB) | 0922164.9 |
| Jul. 2, 2010 | (GB) | 1011192.0 |
| Jul. 26, 2010 | (GB) | 1012499.8 |

(51) Int. Cl.
| G06F 19/00 | (2011.01) |
| G06F 15/00 | (2006.01) |
| G01D 3/032 | (2006.01) |
| G01D 4/00 | (2006.01) |
| G01N 29/44 | (2006.01) |

(52) U.S. Cl.
CPC .......... *G01D 3/032* (2013.01); *G01N 29/4463* (2013.01); *G01D 4/004* (2013.01); *Y02B 90/242* (2013.01); *Y04S 20/322* (2013.01); *Y04S 20/38* (2013.01); *Y02B 70/3266* (2013.01); *Y04S 20/242* (2013.01)

USPC .......... 702/61; 382/275; 702/179; 702/190; 702/191

(58) Field of Classification Search
CPC ..... G01D 3/032; G01D 4/004; Y02B 90/242; Y02B 70/3266; Y04S 20/242; Y04S 20/38; Y04S 20/322; G06K 9/40; G06T 5/10; G06T 5/001; G01N 29/4463
USPC .......... 702/61, 66, 69–71, 73, 79, 190, 191, 702/179; 375/240.1; 348/222.1; 382/275
See application file for complete search history.

(56) References Cited

U.S. PATENT DOCUMENTS

| 4,335,447 A | 6/1982 | Jerrim et al. |
| 4,858,141 A | 8/1989 | Hart et al. |

(Continued)

FOREIGN PATENT DOCUMENTS

| CN | 201210176 | 3/2009 |
| DE | 19535719 | 3/1997 |

(Continued)

OTHER PUBLICATIONS

Intellectual Property Office, Search Report under Section 17 for GB0922164.9, dated Apr. 21, 2011.

(Continued)

*Primary Examiner* — John H Le
(74) *Attorney, Agent, or Firm* — Arent Fox LLP

(57) ABSTRACT

A method and apparatus for carrying out noise reduction in data regarding parameter values including the steps of making a series of measurements of parameter values at times separated by predetermined time intervals, forming a plurality of successive measurements into an array of measurements, performing n successive wavelet transforms on the array of measurements to produce an array of coefficients, comparing the values of the array of coefficients to a threshold value and, selectively changing the values of the coefficients based on their relationship to the threshold, to produce an array of filtered coefficients, and performing n successive inverse wavelet transforms on the array of filtered coefficients to produce an array of filtered measurements.

33 Claims, 5 Drawing Sheets

(56) References Cited

U.S. PATENT DOCUMENTS

| | | | |
|---|---|---|---|
| 5,483,153 | A | 1/1996 | Leeb et al. |
| 5,600,576 | A | 2/1997 | Broadwater et al. |
| 6,195,018 | B1 | 2/2001 | Ragle et al. |
| 6,470,283 | B1 | 10/2002 | Edel |
| 6,507,794 | B1 | 1/2003 | Hubbard et al. |
| 6,826,513 | B1 * | 11/2004 | Kumar et al. ............... 702/185 |
| 6,885,309 | B1 | 4/2005 | Van Heteren |
| 7,146,288 | B1 | 12/2006 | Welch et al. |
| 7,260,272 | B2 * | 8/2007 | Lin et al. ............... 382/275 |
| 7,353,245 | B2 | 4/2008 | Healey |
| 7,379,791 | B2 | 5/2008 | Tamarkin |
| 7,467,170 | B1 | 12/2008 | Chen |
| 7,502,698 | B2 | 3/2009 | Uenou et al. |
| 7,511,609 | B2 | 3/2009 | Hammerschmidt |
| 7,639,129 | B2 | 12/2009 | Bickel et al. |
| 7,693,670 | B2 | 4/2010 | Durling et al. |
| 7,765,034 | B2 | 7/2010 | Gardner |
| 8,103,465 | B2 | 1/2012 | Brzezowski |
| 8,150,950 | B2 | 4/2012 | McQuillan |
| 8,156,055 | B2 | 4/2012 | Shimada |
| 8,201,105 | B2 | 6/2012 | Tabe |
| 8,214,270 | B2 | 7/2012 | Schaefer |
| 8,271,147 | B2 | 9/2012 | Beal |
| 2001/0011278 | A1 | 8/2001 | Shimokawa |
| 2003/0158826 | A1 | 8/2003 | Burke |
| 2004/0008904 | A1 | 1/2004 | Lin |
| 2004/0044713 | A1 | 3/2004 | Healey |
| 2004/0153170 | A1 | 8/2004 | Santacatterina |
| 2005/0057348 | A1 | 3/2005 | Hammerschmidt |
| 2005/0190074 | A1 | 9/2005 | Cumeralto |
| 2007/0013499 | A1 | 1/2007 | Hammerschmidt |
| 2007/0241739 | A1 | 10/2007 | Uenou |
| 2007/0279494 | A1 | 12/2007 | Aman et al. |
| 2008/0001600 | A1 | 1/2008 | deCharms |
| 2008/0079741 | A1 | 4/2008 | Martin |
| 2008/0136409 | A1 | 6/2008 | Sen et al. |
| 2009/0045804 | A1 | 2/2009 | Durling |
| 2009/0066528 | A1 | 3/2009 | Bickel |
| 2009/0088991 | A1 | 4/2009 | Brzezowski et al. |
| 2009/0179642 | A1 | 7/2009 | deCharms |
| 2009/0307178 | A1 | 12/2009 | Kuhns |
| 2010/0152600 | A1 | 6/2010 | Droitcour |
| 2010/0174643 | A1 | 7/2010 | Schaefer |
| 2010/0217450 | A1 | 8/2010 | Beal |
| 2010/0217452 | A1 | 8/2010 | McCord |
| 2011/0004421 | A1 | 1/2011 | Rosewell |
| 2011/0213556 | A1 * | 9/2011 | Yu et al. ............... 702/14 |
| 2012/0197594 | A1 | 8/2012 | Orth |

FOREIGN PATENT DOCUMENTS

| | | |
|---|---|---|
| EP | 295864 | 9/1990 |
| EP | 1309062 | 3/2004 |
| EP | 0863596 | 3/2008 |
| EP | 2026299 | 2/2009 |
| EP | 2237212 | 10/2010 |
| EP | 2290328 | 3/2011 |
| EP | 2141464 | 9/2011 |
| GB | 1012499 | 12/1965 |
| GB | 1107993 | 3/1968 |
| GB | 2300721 | 11/1996 |
| GB | 2420863 | 6/2006 |
| GB | 2409048 | 7/2007 |
| GB | 2461915 | 12/2010 |
| GB | 2472251 | 2/2011 |
| GB | 2473596 | 3/2011 |
| GB | 2471536 | 6/2011 |
| GB | 2490882 | 11/2012 |
| GB | 1108357.3 | 9/2013 |
| JP | 2008202818 | 9/2008 |
| JP | 4976158 | 7/2012 |
| WO | 03026346 | 3/2003 |
| WO | 2008142425 | 11/2008 |
| WO | 2008142431 | 11/2008 |
| WO | 2009014995 | 1/2009 |
| WO | 2009016580 | 5/2009 |
| WO | 2009081407 | 7/2009 |
| WO | 2009103998 | 8/2009 |
| WO | 2010007369 | 3/2010 |
| WO | 2010129414 | 11/2010 |
| WO | 2010106253 | 12/2010 |
| WO | 2011000356 | 1/2011 |
| WO | 2011002735 | 1/2011 |
| WO | 2011058328 | 9/2011 |
| WO | 2012156758 | 11/2012 |

OTHER PUBLICATIONS

XP031881193—Extensible Biosignal Metadata a Model for Physiological Timeseries Data—Brooks D, Sep. 2-6, 2009.

European Search Report & Search Opinion for EP12183390.9, mailed Jan. 25, 2013.

Residential Baseload Energy Use: Concept and Potential for AMI Customers—Nelson et al, year 2008.

XP000336363, "Nonintrusive Appliance Load Monitoring", Hart, George W., Copyright 1992 IEEE.

Younghun Kim, et al., "ViridiScope: Design and Implementation of a Fine Grained Power Monitoring System for Homes", UbiComp 2009, Sep. 30-Oct. 3, 2009, Orlando, Florida, Copyright 2009 ACM 978-1-60558-431-Jul. 9, 2009.

* cited by examiner

| Level 0 | 64 | 48 | 16 | 32 | 56 | 56 | 48 | 24 |
|---|---|---|---|---|---|---|---|---|
| Level 1 | $112/\sqrt{2}$ | $48/\sqrt{2}$ | $112/\sqrt{2}$ | $72/\sqrt{2}$ | $16/\sqrt{2}$ | $-16/\sqrt{2}$ | 0 | $24/\sqrt{2}$ |
| Level 2 | 80 | 92 | 32 | 20 | $16/\sqrt{2}$ | $-16/\sqrt{2}$ | 0 | $24/\sqrt{2}$ |
| Level 3 | $172/\sqrt{2}$ | $-12/\sqrt{2}$ | 32 | 20 | $16/\sqrt{2}$ | $-16/\sqrt{2}$ | 0 | $24/\sqrt{2}$ |

| Level 3 | $172/\sqrt{2}$ | 0 | 0 | 0 | 0 | 0 | 0 | 0 |
|---|---|---|---|---|---|---|---|---|

| Level 3 | 254.9 | -148.8 | 3 | -2.5 | -12.7 | -5.7 | 10.6 | 8.5 |

| Level 3 | 254.9 | -148.8 | 0 | 0 | 0 | 0 | 0 | 0 |

| Reconstructed signal | 37.5 | 37.5 | 37.5 | 37.5 | 142.75 | 142.75 | 142.75 | 142.75 |

METHOD AND APPARATUS FOR NOISE REDUCTION AND DATA COMPRESSION

FIELD OF THE INVENTION

This invention relates to methods, systems, devices and computer code for the noise reduction, compression, storage and transfer of data, particularly data associated with consumption of utilities such as gas, water and electricity, and to transfer the stored utility consumption data for applications such as analysis of household power consumption by an end-user or by a utility supplier, or monitoring occupancy and activity within a household.

BACKGROUND

There is an ongoing and urgent need to reduce consumption of energy and water both for environmental and cost reasons.

A large proportion of the energy and water supplied by utilities suppliers is wasted as a result of inefficiencies such as use of electrical appliances that have poor efficiency or for behavioural reasons such as appliances that are left switched on and so consume electricity even when not in use, or excessive consumption of water. This leads to wastage and increased utilities costs. Moreover, with respect to electricity, electrical energy use in buildings accounts for a very large proportion of all carbon emissions. Demand for utilities can vary dramatically between identical buildings with the same number of occupants, and this suggests that reducing waste through behavioural efficiency is essential. Therefore, efforts are required to change the patterns of utilities use by consumers.

The utilities suppliers recognise three major obstacles to progress in this objective: a shortage of sources of competitive advantage, a lack of detailed understanding of their customers, and a lack of "touch points", i.e. ways of interacting with the customers. Opportunities for differentiation revolve mainly around price and "green" issues, i.e. reduction of environmental impact. The utilities suppliers have very little information about their customers' behaviour since electricity, gas and water meters collect whole house data continuously and are read infrequently.

Meters to measure total consumption of utilities of a household are commonplace for each of gas, electricity and water, however this total is not useful in identifying areas in which efficiencies may be possible (for brevity, we refer herein to a "household", however it will be appreciated that the present invention is not limited to a domestic house but may be applied to any domestic, workplace or other setting that receives its own discrete utilities supplies, in particular mains electricity supply from an electricity grid; water supply; and/or gas supply.).

Apparatus for monitoring consumption of a resource such as electricity supplied on a cable is disclosed in WO 2008/142425. While a meter of this type is beneficial in assisting a user to review energy consumption patterns, when the meter is operated in a high resolution mode, for example measuring power consumption at one second intervals, there is a problem in storing the relatively large amount of power consumption data produced by the meter. Further, when the power consumption data is stored by the meter and subsequently sent to a remote device for display or analysis of resource consumption there is a problem in selecting and transferring the relatively large amount of power consumption data stored by the meter. Further, when the power consumption data is stored by the meter and subsequently sent to a remote device for display or analysis of resource consumption, if communication between meter and the remote device is interrupted there can be problems in selecting and transferring stored power consumption data to the remote device.

It is therefore an object of the invention to provide technical means for compression, storage, recovery and transmission of utilities consumption data in a household.

SUMMARY OF THE INVENTION

According to a first aspect the invention provides a method of noise reduction in data regarding parameter values comprising the steps of:
  making a series of measurements of parameter values at times separated by predetermined time intervals;
  forming an array of measurements of parameter values comprising plural successive measurements of parameter values;
  performing a plurality n of successive wavelet transforms on the array of measurements of parameter values to produce an array of coefficients;
  comparing the values of the array of coefficients to a threshold value and, selectively changing the values of said coefficients based on their relationship to the threshold, to produce an array of filtered coefficients;
  performing n successive inverse wavelet transforms on the array of filtered coefficients to produce an array of filtered measurements.

In a second aspect, the invention provides a data processing apparatus adapted to carry out the method of the first aspect.

In a third aspect, the invention provides a data processing apparatus adapted to reduce noise in data regarding parameter values comprising:
  sensor means adapted to make a series of measurements of parameter values at times separated by predetermined time intervals;
  data processor means adapted to process the series of measurements of parameter values to form an array of measurements of parameter values comprising plural successive measurements of parameter values;
  data processor means adapted to perform a plurality n of successive wavelet transforms on the array of measurements of parameter values to produce an array of coefficients;
  data processor means adapted to compare the values of the array of coefficients to a threshold value and, selectively change the values of said coefficients based on their relationship to the threshold, to produce an array of filtered coefficients;
  data processor means adapted to perform n successive inverse wavelet transforms on the array of filtered coefficients to produce an array of filtered measurements.

In a fourth aspect, the invention provides a data processing apparatus adapted to reduce noise in data regarding electricity consumption comprising:
  sensor means adapted to make a series of measurements of electricity consumption values at times separated by predetermined time intervals;
  data processor means adapted to process the series of measurements of electricity consumption values to form an array of measurements of consumption values comprising plural successive measurements of consumption values;
  data processor means adapted to perform a plurality n of successive wavelet transforms on the array of measurements of consumption values to produce an array of coefficients;

data processor means adapted to compare the values of the array of coefficients to a threshold value and, selectively changing the values of said coefficients based on their relationship to the threshold, to produce an array of filtered coefficients;

data processor means adapted to perform n successive inverse wavelet transforms on the array of filtered coefficients to produce an array of filtered measurements of consumption values.

In a fifth aspect, the invention provides a computer program product adapted to perform the method of the first aspect.

In a sixth aspect, the invention provides a computer program comprising software code adapted to perform the method of the first aspect.

In an eighth aspect, the invention provides a computer program comprising software code adapted to perform steps of:

making a series of measurements of parameter values at times separated by predetermined time intervals;

forming an array of measurements of parameter values comprising plural successive measurements of parameter values;

performing a plurality n of successive wavelet transforms on the array of measurements of parameter values to produce an array of coefficients;

comparing the values of the array of coefficients to a threshold value and, selectively changing the values of said coefficients based on their relationship to the threshold, to produce an array of filtered coefficients;

performing n successive inverse wavelet transforms on the array of filtered coefficients to produce an array of filtered measurements.

In an eighth aspect, the invention provides a computer readable storage medium comprising the program of any one of the fifth to seventh aspects.

In a ninth aspect, the invention provides a computer program product comprising computer readable code according to the eighth aspect.

In a tenth aspect, the invention provides an integrated circuit configured to perform the steps according to the first aspect of the invention.

In an eleventh aspect, the invention provides an article of manufacture comprising: a machine-readable storage medium; and executable program instructions embodied in the machine readable storage medium that when executed by a programmable system causes the system to perform the function of noise reduction in data regarding parameter values comprising the steps of:

making a series of measurements of parameter values at times separated by predetermined time intervals;

forming an array of measurements of parameter values comprising plural successive measurements of parameter values;

performing a plurality n of successive wavelet transforms on the array of measurements of parameter values to produce an array of coefficients;

comparing the values of the array of coefficients to a threshold value and, selectively changing the values of said coefficients based on their relationship to the threshold, to produce an array of filtered coefficients;

performing n successive inverse wavelet transforms on the array of filtered coefficients to produce an array of filtered measurements.

The invention further provides systems, devices, computer-implemented apparatus and articles of manufacture for implementing any of the aforementioned aspects of the invention; computer program code configured to perform the steps according to any one of the aforementioned methods; a computer program product carrying program code configured to perform the steps according to any one of the aforementioned methods; and a computer readable medium carrying the computer program.

DESCRIPTION OF FIGURES

The invention will now be described in detail with reference to the following figures in which.

DETAILED DESCRIPTION OF THE INVENTION

Figure 1:
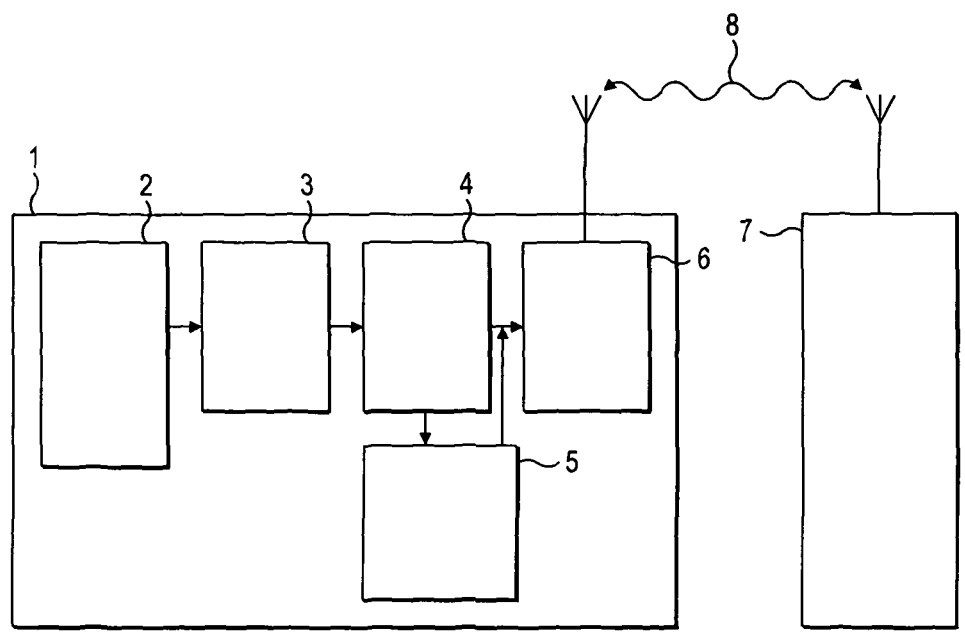
FIG. 1 is a diagram of a smart meter according to the invention.

An example of apparatus for carrying out the method according to the present invention is illustrated in FIG. 1 with respect to electricity consumption.

While the invention is described hereinafter primarily with respect to measurement, analysis and storage of electricity consumption data, it will be appreciated that the same steps may equally be taken using data relating to consumption of gas or water, or other utilities. Further, although the invention is described herein primarily with respect to electrical power measurement, it will be appreciated that other electrical parameters could be measured, for example admittance, frequency, harmonic distortion, voltage, current, etc.

A smart meter 1 comprises a sensing device 2 which measures consumed electrical power for a household, or other setting that receives its own discrete utilities, at fixed interval time points, generating a series of measurements at fixed intervals. A higher frequency of measurement will obviously yield more electricity consumption data, which in turn will generally increase the usefulness and value of the measured data. Typically, for the purposes of the present invention, electricity consumption is measured once every second, at a frequency of 1 Hz.

It will be understood that the amount of power measurement data produced by the sensing device 2 is large, particularly when a relatively high sensing frequency is used, such as 1 Hz. Further, it will be understood that household electricity consumption data is inherently noisy, for example due to random fluctuations in power consumption by household devices and transient effects, so that the measurement data produced by the sensing device 2 is inherently noisy regardless of the performance of the sensing device.

The sensing device 2 measures consumed electrical power by measuring both real power and reactive power. This is captured as two separate streams of data, one stream comprising measurements of real power, and the other stream comprising measurements of reactive power ("real power" and "reactive power" as used herein have the meanings as understood by a skilled person in the art in relation to power supplied to a load from an alternating current source). For simplicity, the two streams of data are represented by a single line in FIG. 1. The power data measurements are two dimensional measurements, where each measurement comprises both a real power measurement and a reactive power measurement made at the same time. It would of course be possible for the real power and reactive power values to be treated or shown as separate streams of measurement. It is also possible to measure other parameters simultaneously with power, for example admittance, voltage, current, etc.

One advantage of measuring both real and reactive power is that, between them, it is possible to measure power demand of most or all appliances. For instance, it may be difficult or impossible to obtain a meaningful measurement of real power for certain appliances such as set-top boxes, however reactive power for these devices can be measured.

The sensing device 2 could be a clamp on energy meter as disclosed in WO 2008/142431.

Although the series of measurements are described as being at fixed intervals this is intended only to indicate that they are at fixed intervals during operation. The sensing device 2 may be able to carry out measurements at a range of different time intervals so that the actual time interval used in a specific application can be set to a suitable value.

As shown in FIG. 1, the power measurements, comprising consumption data readings relating to real and reactive power made at fixed intervals by the sensing device 2, is fed into a noise reduction unit 3.

The noise reduction unit 3 processes the stream of power measurements from the sensing device 2 to reduce noise in the power measurement data. The operation of the noise reduction unit 3 will be discussed in more detail below.

The de-noised power measurement data from the noise reduction unit 3 is then supplied to an event identification device 4, which uses an event identifying algorithm to process the de-noised power measurement data and identify changes in the power consumption values which correspond to events of interest. It will be understood that there are many ways of carrying out such identification, and in any specific application of the invention it will be necessary to select a suitable event identifying algorithm which is appropriate to the fixed interval measurements being made and the events which it is desired to identify. One example of an event identifying algorithm which is suitable for processing fixed interval power measurements to identify events is discussed in detail below.

The event information from the event identification device 4 is then stored in a memory 5. The memory 5 may be any suitable form of data storage device. The event data can then be provided to a wireless transceiver 6 for transmission to remote devices. The event data provided to the wireless transceiver 6 for transmission may be event data which has just been produced by the event identification device 4, or may be taken from the memory 5.

One remote device to which event identification data may be sent is a user display unit 7. The smart meter 1 and the user display unit 7 are arranged for wireless communication thorough a wireless link 8. It is preferred for this to be a bi-directional wireless link, but this is not essential. Suitable wireless communication techniques and wireless communication components to be included in the smart meter 1 and user display unit 7 are well known and need not be discussed in detail here.

The user display unit 7 could be a user display unit as disclosed in WO 2008/142425.

In operation, the smart meter 1 sends the event identification data to the user display unit 7 through the wireless communication link 8. This can be carried out as a "push" type system where the smart meter 1 sends each new event identification data to the user display unit 7 each time said new event identification data is generated and stored in the memory 5, or sends any new event identification data to the user display unit 7 at predetermined times. Alternatively, this can be carried out as a "pull" type system where the user display unit 7 sends a request for data to the smart meter 1 through the wireless communication link 8, and the smart meter 1 responds by sending any new event identification data to the user display unit 7. In this case the user display unit can send the requests at predetermined times, or based on activity at the user display unit 7.

The user display unit 7 may be a data processor able to process and display the event identification data received from the smart meter 1. The user display unit 7 is able to reconstruct the power consumption measured by the smart meter 1 from the received event identification data. This reconstructed power consumption can then be displayed to a user. The reconstructed power consumption can also be used for other purposes, as is known in the art, for example tracking total cumulative power consumption over time or identifying the particular types of appliances being used.

The depiction of different functional parts of the smart meter as different elements in the figures does not indicate that the functions must be necessarily provided by separate physical components.

Figure 2:
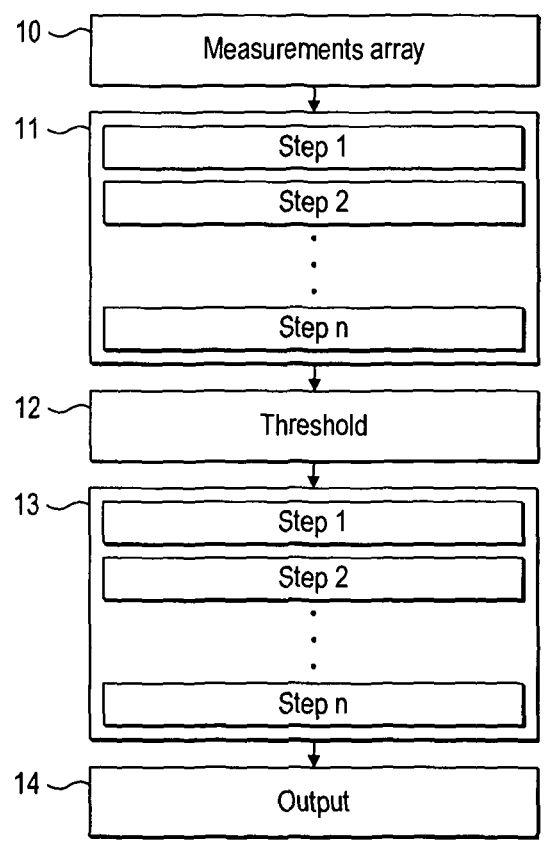
FIG. 2 is a flow diagram of a noise reduction method according to the invention.

As explained above the noise reduction unit 3 processes the stream of power measurements from the sensing device 2 to reduce noise in the power measurement data. An example of the operation of the noise reduction unit 3 according to a first embodiment of the invention will now be explained in detail with reference to the flow chart FIG. 2.

Firstly, in step 10, the noise reduction unit 3 takes the received data, in the described embodiment electricity power consumption measurements from the sensing device 2, and arranges this in an array of measurements. Preferably, the array of measurements comprises $2^n$ measurements. For example, n may be 8, so that the array has $2^8$, that is 256, measurement values.

Then, in step 11, the array of $2^n$ measurements is subjected to n-level wavelet transformation using a Haar Discrete Wavelet Transform. Thus, where the array has 256, $2^8$, samples the array will be subject to an 8-level wavelet transformation. The use of the Haar discrete wavelet transform is preferred, but not essential. Other wavelet transforms can be used.

The discrete wavelet transform represents a one-dimensional signal f of length $2^n$ in terms of shifted versions of a dilated lowpass scaling function $\Phi(x)$, and shifted and dilated versions of a bandpass wavelet function $\Psi(x)$. The Haar wavelet function is given by:

$$\Psi(x) = 1_{[0,1/2)} - 1_{[1/2,1)} \qquad (1)$$

The Haar scaling function is given by:

$$\Phi(x) = 1_{[0,1)} \qquad (2)$$

In these equations $1_{[a,b)}$ denotes the characteristic function, equal to 1 on [a,b) and zero everywhere else.

The signal f can be expanded in this basis, giving:

$$f = \sum_i c_i^n \Phi_i^n(x) + \sum_j \sum_i d_i^j \Psi_i^j(x) \qquad (3)$$

The multi-level normalized scaling functions is defined to be:

$$\Phi_i^j(x) = 2^{j/2} \Phi(2^j x - i) \qquad (4)$$

While the multi-level normalized wavelet function is defined to be:

$$\Psi_i^j(x) = 2^{j/2} \Psi(2^j x - i) \qquad (5)$$

Where $i=0, \ldots 2^j-1$ and $j=0, \ldots, n$. The scaling coefficients $c_i^j$ and wavelet coefficients $d_i^j$ at a level j can be computed from the coefficients $c_i^{j+1}$ at level j+1 and vice-versa using:

$$c_i^j = (c_{2i}^{j+1} + c_{2i-1}^{j+1})/\sqrt{2} \qquad (6)$$

$$d_i^j = (c_{2i}^{j+1} - c_{2i-1}^{j+1})/\sqrt{2} \qquad (7)$$

After completion of the n-level Haar wavelet transform the resulting coefficients contain all of the information of the original power measurements and could, in principle, be used to reconstruct them by reversing the process.

In one embodiment of the present invention the set of coefficients output from the final stage, that is the nth stage, of the n-level wavelet compression is subject to a hard threshold filtering in step 12. For example, where the array has 256, $2^8$, samples the hard threshold filtering is carried out on the wavelet coefficients output by the 8$^{th}$ level wavelet compression.

The hard threshold filtering compares the coefficients to a threshold. All of the coefficients having a value below the threshold then have their value set to zero. This is referred to as wavelet shrinkage, or de-noising.

This hard threshold filtering uses a threshold T set according to:

$$T = \sqrt{2 \ln(m)} \mathrm{SMAD}(d_i^{n-1}) \qquad (8)$$

Where m is the number of measurements in the original set of power measurements, and SMAD ($d_i^{n-1}$) is the scaled median absolute deviation computed from the first level high pass wavelet coefficients, that is, the median of the absolute values of the first level high pass, or detail, wavelet coefficients, given by $d_{0, \ldots, 3}^2$.

Thus, all of the wavelet coefficients at the nth, that is, the last, stage wavelet compression having an absolute value of less than T are set to have a value of zero.

This hard threshold filtering has the effect of removing noise from the power measurement data. The hard threshold filtering using the threshold T as described above has the effect of measuring the entropy in the power measurement signal and removing the high entropy noise parts of the signal.

The hard threshold filtered coefficients are then subjected to an n-level, or n-step, inverse discrete wavelet transform, also known as reverse wavelet transformation, using the reverse Haar Transform in step 13. Thus, where the array has 256, $2^8$, samples the array will be subject to an 8-level wavelet reverse transformation.

As explained above, absent the hard threshold filtering the n-level reverse transformation would have regenerated the original set of $2^n$ power measurements. However, because the nth level wavelet coefficients were subjected to wavelet shrinkage by the hard threshold filtering, the output of the nth level reverse wavelet transformation is a reconstructed version of the original power measurements which has been de-noised so that the amount of noise in the power measurements is reduced.

This de-noised power measurements are then output from the noise reduction unit 3 in step 14 and supplied to the event identification device 4.

In addition to the threshold setting method described above, it may be preferred to also set a minimum level for the threshold, and to set the threshold value to this minimum level when the calculated threshold value T is below the minimum level. The setting of a minimum threshold level can be useful to reduce low level noise which is below the smallest amplitude expected to be a real signal corresponding to an event of interest.

The above example describes the use of a hard threshold. Although this is generally effective, other types of threshold may alternatively be used, if preferred. Further, other options for setting the threshold could be used as alternatives to that set out in equation (8).

The above example describes the use of the Haar discrete wavelet transform. Other types of wavelet transform can alternatively be used. In general, the wavelet transform used can be selected taking into account the processing which is to be applied after the de-noising process, to match the properties of the de-noised signal with the requirements of the subsequent processing. The wavelet transform used can also be selected taking into account the expected properties of the changes in the input signal which it is desired to detect, and the expected properties of noise, and any other undesired signal components, which it is desired to remove.

A worked example of the operation of the noise reduction method according to the invention is discussed below.

The noise reduction method according to the invention has the advantage that it is automatically adaptive to the level of ambient noise in the signal, and removes the noise without affecting the real signal data.

The method of determining the threshold for the filtering described above is not essential. The formula used to calculate the threshold can be changed and configured to adjust the level of filtering applied, as required in different applications.

The use of a Haar wavelet transform together with adaptive hard threshold filtering as described above is particularly effective when used in conjunction with an event identification process because this removes noise while preserving the sharp edges and corners in the measurement data which are used for event identification. In contrast, conventional filtering of the power measurements in order to remove noise would tend to smooth out the sharp edges and corners and replace them with smoother and harder to identify features.

The noise reduction method according to the invention is much more effective than attempting to remove noise after the event detection. Further, unlike a conventional approach of noise reduction by filtering, the noise reduction method according to the invention will not affect the corners and edges in the data which are used in the event detection.

The event identifying device 4 identifies events by using an event identifying algorithm, which processes the de-noised power measurements and compares changes in values of parameters of the de-noised power measurements to selected criteria and thresholds in order to identify changes in the values which correspond to events of interest. It will be understood that there are many ways of carrying out such identification, and in any specific application of the invention it will be necessary to select a suitable event identifying algorithm which is appropriate to the fixed interval measurements being made and the events which it is desired to identify. One example of an event identifying algorithm which is suitable for processing fixed interval power measurements to identify events is discussed in detail below.

Since event detection identifies changes in measured parameters it is necessary to ensure that the measurements at the beginning and end of successive arrays of $2^n$ measurements processed by the noise reduction unit 3 are compared with both preceding and succeeding measurements by the event identifying device to ensure that no changes or events are missed by the event identifying device as a result of the change or event occurring at or close to the boundary between successive arrays. This can be done by ensuring that the end measurements in time in each array of $2^n$ measurements processed are duplicated as the beginning elements in time in the next array of $2^n$ measurements processed. The number of end and beginning measurements duplicated in successive processed arrays of measurements will depend on the properties of the event identifying technique used.

When the event identifying device 4 identifies an event it generates a respective event measurement corresponding to the event and comprising the relevant measured event parameter values together with a timestamp which indicates the time at which the event took place. Accordingly, the event identifying device 4 generates as an output a series of event measurements at variable intervals. It will be understood that the intervals between the event measurements in the series of event measurements are variable because the timing of the event measurements depends on the timing of the identified events. Since the identified events are "real world" events their timing is inherently variable.

In the described embodiment each variable interval event measurement comprises the real and reactive power consumption value measurements at the time of the identified event together with the corresponding timestamp. Thus, the event parameter values of the event measurements are derived from the de-noised power measurements by selection. It will be understood that other forms of derivation are possible. The form of derivation used may be selected based upon the details of the event identifying algorithm.

Optionally, each variable interval event measurement can also comprise further parameter values relating to the event and produced during the processing. For example, the further parameter values could be value measurements of admittance, frequency, harmonic distortion, or voltage. In practice, whether such further parameter values are desired, and if so, what the further parameters are, will depend upon what processing is applied and the intended use of the variable interval event measurement in each case.

As stated above, each event measurement corresponds to a respective event. It will be understood that the generation of each event measurement implicitly identifies that some event has taken place. However, it is not required that the type of the event is identified by the event measurement, although this could optionally be done.

The event identifying device may be provided by software running on a general purpose processor of the smart meter. Alternatively, the event identifying device may be provided by hardware in the form of an application specific integrated circuit (ASIC) in the smart meter.

The series of event measurements at variable intervals from the event identifying device 4 is fed to the memory 5 where the event measurements, including their respective timestamps, are stored.

In practice, it has been found that most of the power measurements from the power sensor 1 are not associated with events of interest. As a result, use of the present invention reduces the amount of data which must be stored in order to allow power consumption to be tracked over time, and in order to allow the power consumption history to be reproduced from the stored data. It is possible that over some short periods when there are an unusually large number of events there may be no reduction in the amount of data which must be stored. However, even in these cases, there will still be an overall reduction over longer periods. In practice it has been found that a compression ratio in the range 81% to 99%, with an average of 93.7% can be achieved.

Thus, the amount of data recording the power consumption can be compressed. This data compression is a lossy compression because the data regarding fixed interval measurements which are not associated with an event of interest is not recorded.

The degree of compression will depend, among other things, on the number, or frequency, of events relative to the number, or frequency, of fixed interval measurements. Thus, for any specific number of events, the degree of compression will increase as the time interval between the fixed interval measurements decreases, that is, as their frequency increases.

Noise Reduction

An example of the working of the noise reduction algorithm for n=3 will now be discussed in detail with reference to FIG. 3.

In the example we start with 8 power measurement values, that is n=3, in this case the measurements are power measurements including random noise which form a signal f=[64, 48, 16, 32, 56, 56, 48, 42]. Accordingly, as shown in FIG. 3 the initial array of 8 power measurement values, the level zero coefficient values are $c_{0,\ldots,7}^3 = [64, 48, 16, 32, 56, 56, 48, 24]$. This array of zero level values is then subject to a Haar discrete wavelet transform to generate a set of eight level 1 coefficients as shown.

The four level 1, or first level, wavelet, high pass, coefficients are:

$$d_{0,\ldots,n}^2 = [16, -16, 0, 24]/\sqrt{2} \tag{10}$$

The four level 1, or first level, scaling, low pass, coefficients are:

$$c_{0,\ldots,n}^2 [112, 48, 112, 74]/\sqrt{2} \tag{11}$$

Then, the four level 1, or first level, scaling coefficients given in equation 11 are subject to a Haar discrete wavelet transform to generate a set of four level 2, or second level, coefficients as shown.

The two level 2, or second level, wavelet coefficients are:

$$d_{0,1}^1 = [32, 20] \tag{12}$$

The two level 2, or second level, scaling coefficients are:

$$c_{0,1}^1 = [80, 92] \tag{13}$$

Then, the two level 2, or second level, scaling coefficients are subject to a Haar discrete wavelet transform to generate a set of two level 3, or third level, coefficients as shown.

The level 3, or third level, wavelet coefficient is:

$$d_0^0 = -12/\sqrt{2} \tag{14}$$

The level 3, or third level, scaling coefficient is:

$$c_0^0 = 172/\sqrt{2} \tag{15}$$

In this example where n=3, the initial array of measurements could be written in the Haar wavelet basis as:

$$f = c_0^0 \Phi_0^0 + d_0^0 \Psi_0^0 + d_0^1 \Psi_0^1 + d_1^1 \Psi_1^1 + d_0^2 \Psi_0^2 + d_1^2 \Psi_1^2 + d_2^2 \Psi_2^2 + d_3^2 \Psi_3^2 \tag{9}$$

Another way of looking at this process is from a filter perspective, where the operations to calculate the coefficients may be seen to be averaging and differencing operations. Accordingly, the first level scaling coefficients are the averages of the pairwise data array entries and the first level wavelet coefficients are the results of finding the differences between the pairwise data array entries. Applying these averaging and differencing operations will provide the first level wavelet and scaling coefficients in FIG. 3.

If we then calculate the hard threshold T according to equation (8) from the first wavelet level coefficients we find that T=34.2. Then, if all of the third level coefficients having an absolute value less than 34.2 are identified and their value set to zero, the hard threshold filtered third level coefficients are as shown in FIG. 4.

When three levels of reverse wavelet transformation are applied to this filtered third level value it is found that the resulting filtered level zero power measurements are a constant value of 43. All of the random noise-like fluctuations have been removed.

Figures 3, 4, 5:
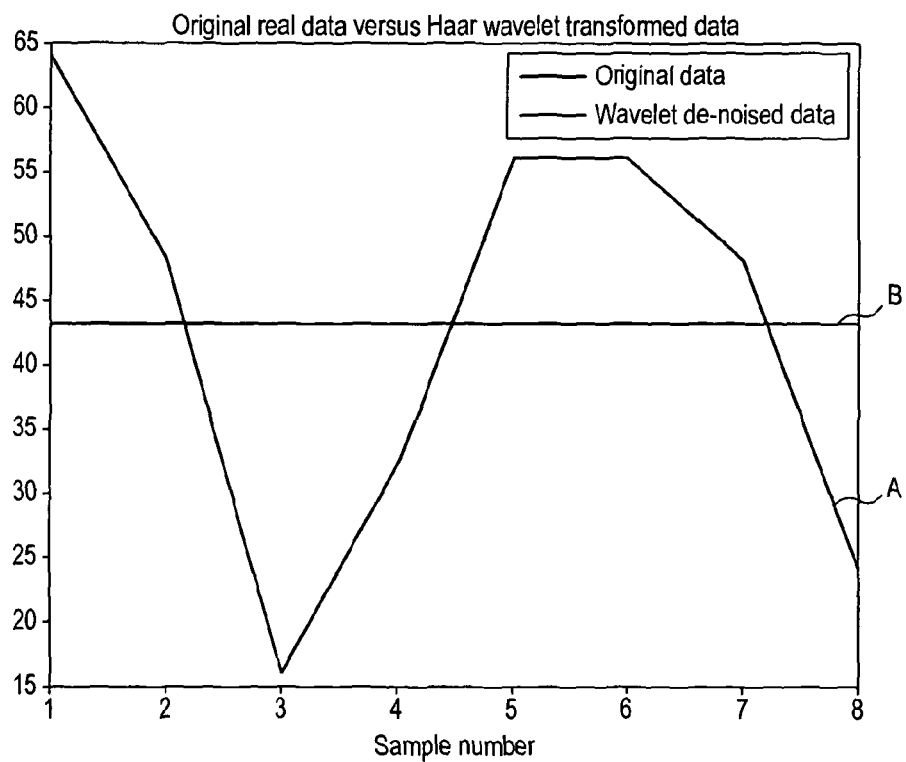
FIG. 3 is a table showing an example of operation of the noise reduction method according to the invention.
FIG. 4 is a table showing an example of operation of the noise reduction method according to the invention.
FIG. 5 is a graph showing the effect of the noise reduction of FIGS. 3 and 4.

This is shown in FIG. 5, which shows a graph of the original noisy signal A and the regenerated filtered and denoised signal B.

As a further example, consider a power measurement signal which includes 20 W noise and includes a step change of 100 W. This can be simulated by a signal f=[30, 48, 32, 40, 149, 134, 150, 138]. Applying three levels of Haar discrete wavelet transformation as before gives third level coefficients as shown in FIG. 6.

Figures 6, 7, 8, 9:
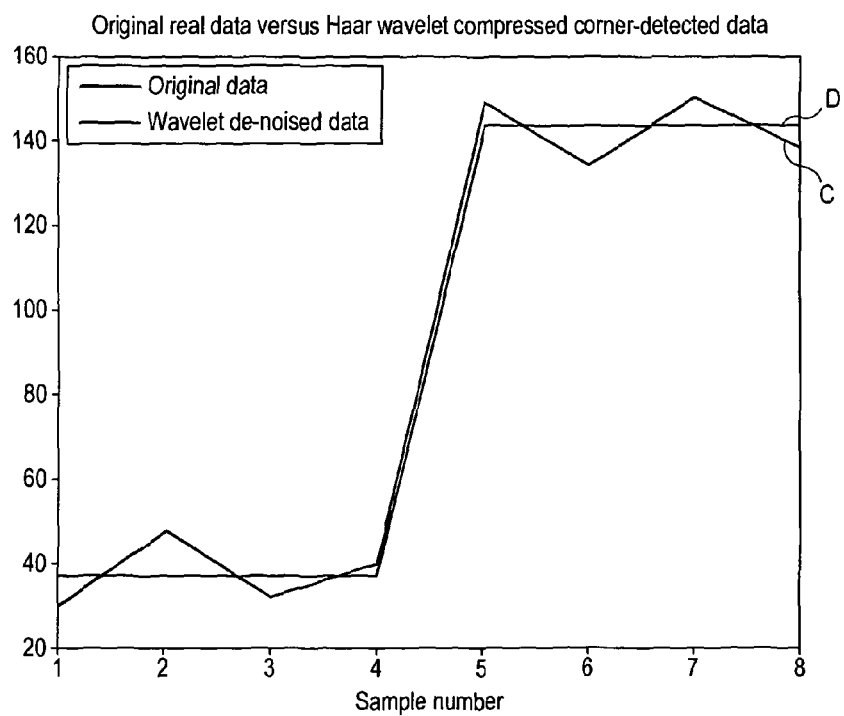
FIG. 6 is a table showing an example of operation of the noise reduction method according to the invention.
FIG. 7 is a table showing an example of operation of the noise reduction method according to the invention.
FIG. 8 is a table showing an example of operation of the noise reduction method according to the invention.
FIG. 9 is a graph showing the effect of the noise reduction of FIGS. 6 to 8.

In this case the threshold can be calculated as T=35.3, and setting all wavelet coefficients with absolute values below this to zero gives a set of filtered third level coefficients as shown in FIG. 7. If these filtered coefficients are subject to three levels of reverse wavelet transformation the reconstructed filtered signal shown in FIG. 8 is produced. As can be understood in FIG. 8, the noise has been removed from this signal, but the 100 W step change is still present and sharply defined.

This is shown in FIG. 9, which shows a graph of the original noisy signal C and the regenerated filtered and denoised signal D.

A specific example of an event detection algorithm, referred to hereinafter as a "corner detection algorithm", which can be used in the present invention will now be described in detail.

Corner Detection

Figure 10:
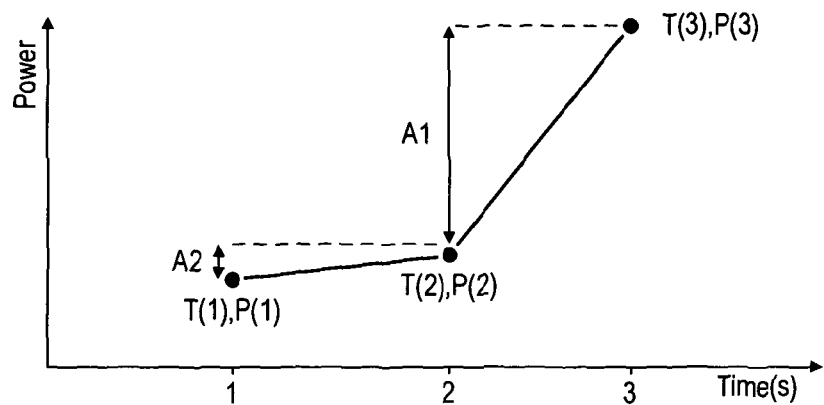
FIG. 10 illustrates the identification of "corners" in electricity consumption data.

The operation of the corner detection algorithm is illustrated schematically in FIG. 10. The compression algorithm identifies "corners" in power demand by identifying differences in the gradient representing rate of change in power from one fixed interval time point to the next. These corners in power demand are regarded as events of interest in the present invention.

A point at which there is change in gradient between two successive time intervals (identified as T(2), P(2)) is marked as a "corner" if that change is greater than a predetermined threshold. This is done by measuring the power difference between points T(3), P(3) and T(2), P(2) and between T(2), P(2) and T(1), P(1) to give values A1 and A2 respectively. If the difference B between A1 and A2 exceeds a predetermined value Tol1 then a corner is marked.

Thus, three successive measurements are required to identify a corner with this technique. Accordingly, to ensure that corners close to the boundary between successive arrays of the noise reduction method are not missed the final two end measurements in time in each array of measurements processed in the noise reduction method are duplicated as the first two beginning elements in time in the next array of measurements processed. Thus, in the specific example discussed above, the last two entries in each array of $2^n$ measurements are duplicated as the first two entries in the following array of $2^n$ measurements.

Figure 12:
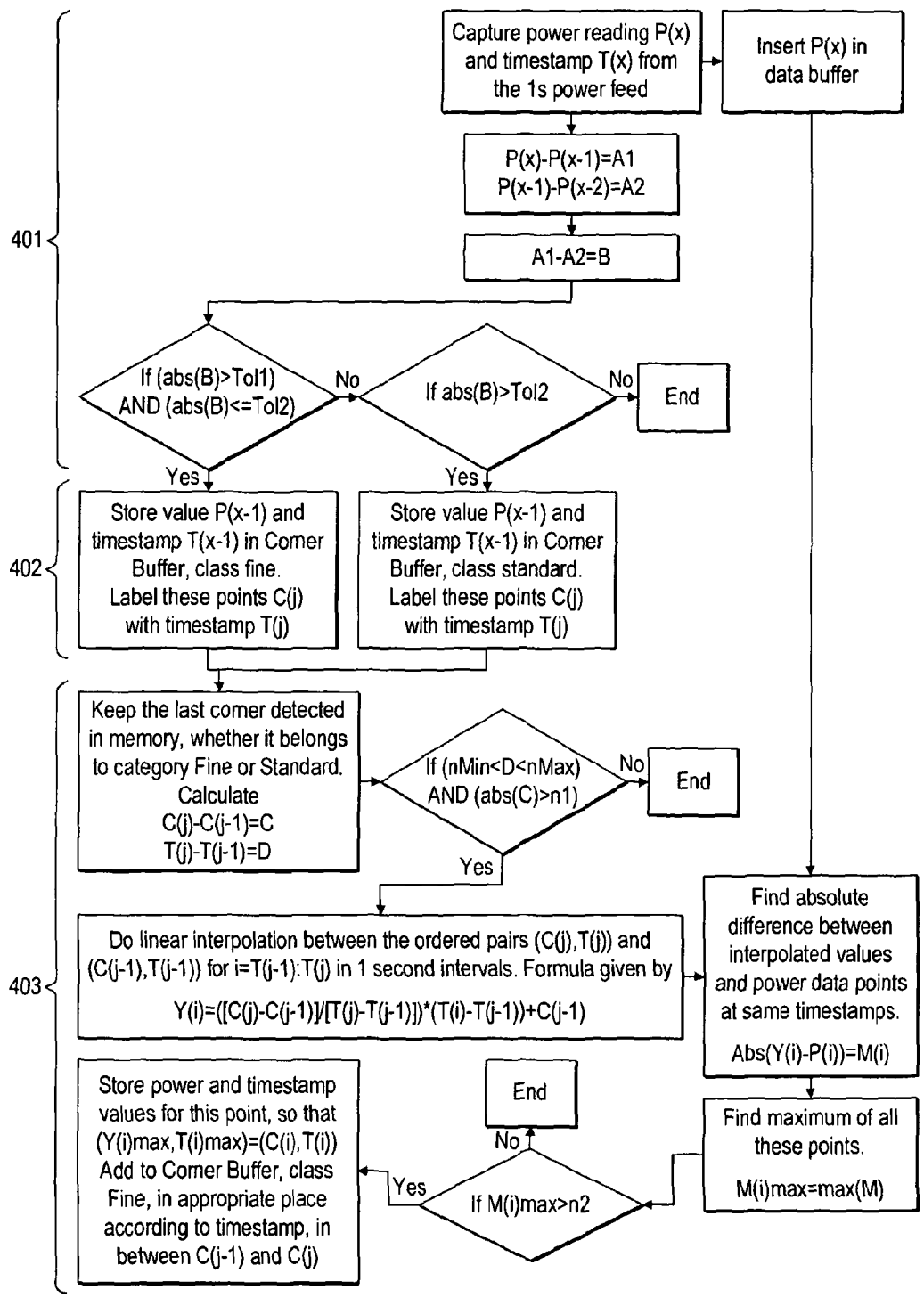
FIG. 12 is a flowchart illustrating the corner detection algorithm.

The operation of the algorithm is illustrated in more detail in FIG. 12 in which:

T(x), T(i) and T(j) represent 32 Bit timestamps
C(x), C(j) and Y(i) represent 16 Bit power readings at a corner
Tol1, Tol2 represent integer numerical values (0-100)
A1, A2, B represent 16 Bit power reading differences
n1, nMax, nMin, n2 represent 16 Bit numerical values
M(i), M(i)max represent 16 Bit numerical values Section 401 of FIG. 12 illustrates identification of corners as described above with reference to FIG. 3.

Section 402 of FIG. 12 illustrates the classification of corners into "Standard" and "Fine" classes depending, respectively, on whether B is greater than predetermined values Tol1 and Tol2 or greater than Tol1 only.

The skilled person will understand how to select the value of the threshold for marking a point as a corner, and the specific value will vary from case to case.

By measuring and identifying these corners in the fixed interval power measurements, and outputting data regarding these corners, the corresponding parameter values and the associated timestamp values, the series of event measurements 12 at variable intervals is produced.

The series of event measurements at variable intervals allows an electricity consumption history to be generated, either in real time from the event measurements as they are produced, or retrospectively from stored event measurements, such as the event measurements stored in the memory 5.

Correction

The series of event measurements at variable intervals generated as described above with respect to FIG. 10 and sections 401 and 402 of FIG. 12 contains the majority of corners, however a correction may be applied to identify one or more corners that may have been missed.

Figure 11:
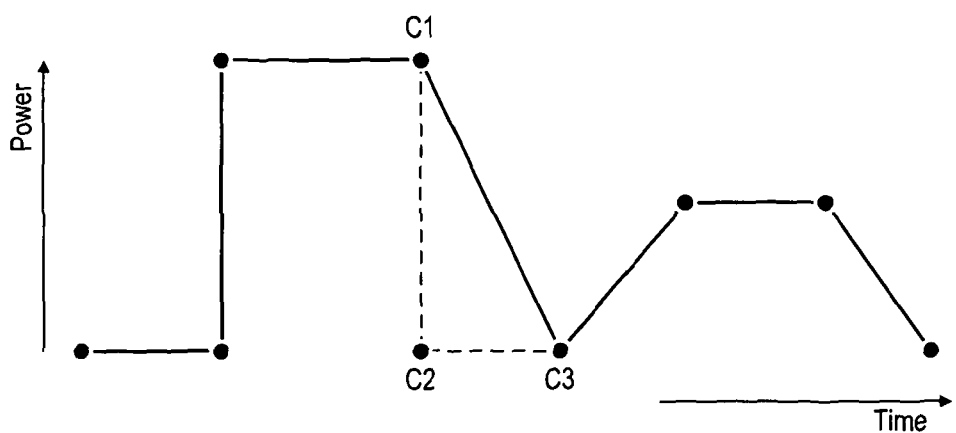
FIG. 11 illustrates schematically the identification of missing corners.

This is illustrated in FIG. 11 which shows a corner C(2) between corners C(1) and C(3) that has been missed by the corner detection algorithm.

A missing corner may be identified if both the power difference (power at C1 minus power at C2) and the time difference (time at C1 minus time at C2) fall outside defined values as illustrated in section 403 of FIG. 12.

In this event, a linear interpolation may be conducted to identify any missing corners, as illustrated in Section 403 of FIG. 12. Referring to FIG. 11, missing corner C3 should be inserted at the point giving the most acute angle between lines C1–C2 and C2–C3.

The use of the utilities consumption data noise reduction and compression method according to the present invention provides the advantage that noise in the raw measured data can be removed without impairing the compression. Further, the use of the utilities consumption data noise reduction and compression method according to the present invention provides the advantage that for any selected interval between the fixed interval power measurements the amount of data which must be stored at the smart meter 1, and the amount of data which must be transferred from the smart meter 1 to the user display device 7 can be reduced. Further, the use of the utilities consumption data noise reduction and compression method according to the present invention provides the advantage that the amount of data which must be stored and transferred is not directly related to the frequency of the fixed interval power measurements. Accordingly, the frequency, or interval, of the fixed interval power measurements in any specific application can be selected as required to provide the desired time resolution without having to consider whether the amount of data which will need to be stored or transmitted will be excessive.

The exemplary embodiment described above explains one example of how the present invention may be carried out. It will be understood that further data processing may be carried out in addition to that described. For example, there may be some pre-processing of the power measurements, such as filtering to remove noise, before the event identification is carried out. Further, in addition to the above described lossy compression techniques according to the present invention, the data to be stored or transmitted may also be compressed using a conventional lossless compression technique.

It should be understood that the available bandwidth or data transfer rate from the smart meter 1 to the user display device 7 via the wireless communication link 8 may be relatively low or costly so that the transfer of large amounts of data is highly undesirable.

It will usually be preferred for the user display unit 7 to be in substantially continuous wireless contact with the smart meter 1 so that measurements made by the smart meter 1 are transferred to the user display unit 7 in real time as they are made. However, in some circumstances it may be necessary to transfer historic power consumption data, that is previously recorded power consumption data, from the smart meter 1 to the user display unit 7. This will be necessary if the user display unit 7 has been temporarily out of contact with the smart meter 1, and the power consumption data missed during the lost contact period must be transferred. Further, when a new user display unit 7 is installed to an existing smart meter 1, the user display unit 7 will of course have previously been out of contact with the smart meter 1, and historic power consumption data for a previous period must be transferred. The length of this previous period will vary from case to case. Further, if a particular previous period of time is of interest to a user it may be necessary to transfer historic power consumption data for this period if it has not been stored in the user display device.

Using a conventional meter in which only a cumulative total of consumed energy is stored, these data transfers could not be made as the required data would not be present on the meter. Further, using a known smart meter where power measurement readings are stored at fixed intervals it can be very difficult to provide the desired information to the user display device because of the every large amount of power readings which must be transferred, and also because it may be difficult or impossible to determine what time any particular power reading corresponds without working back from the most recent data through all of the series of historic data in sequence, which will require a large amount of processing.

These problems can be overcome by the present invention because the utilities consumption data compression method of the present invention dramatically reduces the amount of information that must be transferred, and because each variable interval event measurement is stored in association with a timestamp so that the specific time of the measurement can be easily determined.

In the above described embodiment electrical power consumption is measured. It will be understood that power and energy are closely related so that the skilled person will readily understand how to use the power consumption values to determine values of consumed energy. Further, it will be understood that measured power consumption can be expressed or defined directly in terms of power, or indirectly in terms of the amount of energy consumed since the preceding measurement, provided that the time between the successive measurements is known.

The above description describes the processing, compression, storage and delivery of a single data stream of electrical power consumption data. This is only by way of example, the present invention is also applicable to other parameters. Further, the smart meter may generate, process, compress, store and deliver multiple data streams relating to respective different parameters, and each data stream can be independently processed, stored and queried. The different parameters may be measured at the same or different fixed measurement intervals, as appropriate to the different parameters.

The different data streams relating to the different parameters may be separately processed to identify events and stored separately. Alternatively, the fixed interval measurements in the different data streams relating to the different parameters may be processed together to identify events and/or stored together. For example, a smart meter measuring real power, reactive power, voltage, current and frequency of an electrical utility supply at respective fixed intervals could process the real power and reactive power to identify events, and when an event is identified store the real power and reactive power values, and the voltage, current and frequency values, together with the timestamp.

Typically, the user display device is a domestic client display able to provide real time and historical displays and analyses of utility consumption to a domestic user.

The user display device may be portable. In this case the user display device may often be out of contact with the smart meter.

In the above described embodiment of the invention the user display device is connected to the smart meter by a wireless communication link. As an alternative it would be possible for the user display device to be connected to the smart meter by a direct wired connection. The user display device could even be combined with the smart meter in a single unit.

The above described embodiment describes the invention as employed by a smart meter in communication with a user display device. The smart meter could additionally, or alternatively, be connected to other client devices such as a user PC, a utility supplier billing computer, or third party data collection centre, either directly. Similarly, the user display device could be connected to client devices such as a user PC, a utility supplier billing computer, or third party data collection centre. These connections can conveniently be made through a user internet connection. The smart meter will usually have an advanced metering infrastructure (AMI) or automatic metering system (AMR) data connection, but it will usually be too costly to use these to transfer data to client devices.

In the above described embodiment of the invention a single user display device is connected to a single smart meter by a wireless communication link. As an alternative it would be possible for a single user display device to be connected to multiple smart meters. The multiple smart meters could measure different utilities, and/or supply of the same utility to different households, or other settings that receives their own discrete utilities, of interest to the user. As another alternative it would be possible for multiple user display devices, or other client devices, to be connected to a single smart meter. In this case, data requested by the different devices can be delivered as a series of responses.

The invention has been discussed primarily with respect to consumption of electricity, however it will be appreciated that the methods described herein can equally be applied to consumption of water or gas supplied to a household.

Consumption of water and gas can be measured using techniques that are well known to the skilled person, for example based on use of water and gas meters. Water and gas consumption, in particular water consumption, may be measured at a lower rate, for example at least once every 300 seconds or at least once every 60 seconds, in order to generate water consumption data that may be used to identify events associated with consumption of water. The rate of flow of water or gas at each time interval may be measured, along with the total volume consumed over time in a manner analogous to power and energy measurements of electricity consumption. Additionally or alternatively, water and gas consumption may be measured at measurement points after intervals of volume consumption rather than intervals of time, for example a measurement of time elapsed for each unit volume (e.g. liter) of water to be consumed.

The apparatus described above may be implemented at least in part in software. Those skilled in the art will appreciate that the apparatus described above may be implemented using general purpose computer equipment or using bespoke equipment.

The hardware elements, operating systems and programming languages of such computers are conventional in nature, and it is presumed that those skilled in the art are adequately familiar therewith. Of course, the server functions may be implemented in a distributed fashion on a number of similar platforms, to distribute the processing load.

Here, aspects of the methods and apparatuses described herein can be executed on a mobile station and on a computing device such as a server. Program aspects of the technology can be thought of as "products" or "articles of manufacture" typically in the form of executable code and/or associated data that is carried on or embodied in a type of machine readable medium. "Storage" type media include any or all of the memory of the mobile stations, computers, processors or the like, or associated modules thereof, such as various semiconductor memories, tape drives, disk drives, and the like, which may provide storage at any time for the software programming. All or portions of the software may at times be communicated through the Internet or various other telecommunications networks. Such communications, for example, may enable loading of the software from one computer or processor into another computer or processor. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links or the like, also may be considered as media bearing the software. As used herein, unless restricted to tangible non-transitory "storage" media, terms such as computer or machine "readable medium" refer to any medium that participates in providing instructions to a processor for execution.

Hence, a machine readable medium may take many forms, including but not limited to, a tangible storage carrier, a carrier wave medium or physical transaction medium. Non-volatile storage media include, for example, optical or magnetic disks, such as any of the storage devices in computer(s) or the like, such as may be used to implement the encoder, the decoder, etc. shown in the drawings. Volatile storage media include dynamic memory, such as the main memory of a computer platform. Tangible transmission media include coaxial cables; copper wire and fiber optics, including the wires that comprise the bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

Those skilled in the art will appreciate that while the foregoing has described what are considered to be the best mode and, where appropriate, other modes of performing the invention, the invention should not be limited to specific apparatus configurations or method steps disclosed in this description of the preferred embodiment. It is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings. Those skilled in the art will recognize that the invention has a broad range of applications, and that the embodiments may take a wide range of modifications without departing from the inventive concept as defined in the appended claims.

Although the present invention has been described in terms of specific exemplary embodiments, it will be appreciated that various modifications, alterations and/or combinations of features disclosed herein will be apparent to those skilled in the art without departing from the spirit and scope of the invention as set forth in the following claims.

The invention claimed is:

1. A method implemented by a processor for noise reduction in data regarding parameter values, the method comprising the steps of:
    making a series of measurements of parameter values at times separated by predetermined time intervals;
    forming an array of measurements of parameter values comprising plural successive measurements of parameter values;
    performing a plurality n of successive wavelet transforms on the array of measurements of parameter values to produce an array of coefficients;
    comparing the values of the array of coefficients to a threshold value and, selectively changing the values of said coefficients based on their relationship to the threshold, to produce an array of filtered coefficients; and
    performing n successive inverse wavelet transforms on the array of filtered coefficients to produce an array of filtered measurements.

2. The method of claim 1, wherein the array of measurements of parameter values, the array of coefficients, the array of filtered coefficients and the array of filtered measurements all have the same number of entries.

3. The method of claim 2, wherein each of said arrays has $2^n$ entries.

4. The method of claim 1, wherein the values of all of the wavelet coefficients of the array of coefficients are compared to the threshold value and selectively changed.

5. The method of claim 4, wherein the values of all of the wavelet coefficients of the array of coefficients are compared to the threshold value and, for each wavelet coefficient having an absolute value smaller than the threshold value, setting the value of said coefficients to be zero, to produce the array of filtered coefficients.

6. The method of claim 1, wherein each wavelet transform is a Haar discrete wavelet transform.

7. The method of claim 6, wherein each inverse wavelet transform is an inverse Haar discrete wavelet transform.

8. The method according to claim 1, where the threshold is derived from the wavelet coefficients produced by the first of the n successive wavelet transforms.

9. The method according to claim 8, where the threshold is derived from the scaled median absolute deviation of the wavelet coefficients produced by the first of the n successive wavelet transforms.

10. The method according to claim 9, where the threshold value T is defined by the equation $$T = \sqrt{2 \ln(m) \mathrm{SMAD}(d_i^{n-1})}$$

where m is the number of measurements in the original array of measurements, and SMAD ($d_i^{n-1}$) is the scaled median absolute deviation computed from the wavelet coefficients produced by the first of the successive wavelet transforms.

11. The method according to claim 1, where the series of measurements of parameter values are formed into a series of arrays of measurements of parameter values, each of $2^n$ successive measurements of parameter values.

12. The method according to claim 11, where one or more final measurements of parameter values in each array of measurements of parameter values are duplicated as the one or more beginning measurements of parameter values in the next successive array of measurements of parameter values.

13. The method according to claim 12, where two final measurements of parameter values in each array of measurements of parameter values are duplicated as the two beginning measurements of parameter values in the next successive array of measurements of parameter values.

14. The method according to claim 1, and further comprising the step of:
processing the array of $2^n$ filtered measurements to identify events at different times.

15. The method according to claim 14, and further comprising the steps of:
generating a further series of filtered measurements of parameter values at each of said different times; and
storing each of said further series of filtered measurements of parameter values in association with said respective different time.

16. The method according to claim 15, wherein said further series of filtered measurements of parameter values are derived from said filtered measurements.

17. The method according to claim 16, wherein said further series of measurements of parameter values are derived from said filtered measurements using a selection process.

18. The method according to claim 15, further comprising transmitting the stored measurements of parameter values and associated times to a data processor.

19. The method according to claim 18, wherein the stored measurements of parameter values and associated times are transmitted by wired or wireless transmission.

20. The method according to claim 18, wherein the data processor is a user display device.

21. The method according to claim 20, wherein the user display device is a domestic user display device.

22. The method according to claim 14, wherein the processing comprises determining a gradient of change of parameter value between each consecutive filtered measurement and identifying as events times where a change in successive gradients exceeds a threshold value.

23. The method according to any 1, wherein said predetermined time intervals are fixed time intervals.

24. The method according to claim 1, wherein the intervals between measurements is in the range 0.01 to 60 seconds.

25. The method according to claim 24, wherein the intervals between measurements are 1 second.

26. The method according to claim 1, wherein said parameter values are utilities consumption values.

27. The method according to claim 26, wherein the utility is selected from gas, electricity and water.

28. The method according to claim 27, wherein the utility is electricity and the electricity consumption values include measured values of real power, reactive power, or both reactive power and real power.

29. An apparatus adapted to reduce noise in data regarding electricity consumption comprising:
means for making a series of measurements of electricity consumption values at times separated by predetermined time intervals;
means for processing the series of measurements of electricity consumption values to form an array of measurements of consumption values comprising plural successive measurements of consumption values;
means for performing a plurality n of successive wavelet transforms on the array of measurements of consumption values to produce an array of coefficients;
means for comparing the values of the array of coefficients to a threshold value and, selectively change the value of said coefficients based on their relationship to the threshold, to produce an array of filtered coefficients; and
means for performing n successive inverse wavelet transforms on the array of filtered coefficients to produce an array of filtered measurements of consumption value.

30. A system comprising:
an apparatus adapted to reduce noise in data regarding electricity consumption comprising:
means for making a series of measurements of electricity consumption values at times separated by predetermined time intervals;
means for processing the series of measurements of electricity consumption values to form an array of measurements of consumption values comprising plural successive measurements of consumption values;
means for performing a plurality n of successive wavelet transforms on the array of measurements of consumption values to produce an array of coefficients;
means for comparing the values of the array of coefficients to a threshold value and, selectively change the value of said coefficients based on their relationship to the threshold, to produce an array of filtered coefficients; and
means for performing n successive inverse wavelet transforms on the array of filtered coefficients to produce an array of filtered measurements of consumption value; and
a data processor adapted to receive transmitted stored measurements of parameter values and associated times.

31. The system according to claim 30, wherein the data processor is a user display device.

32. The system according to claim 31, wherein the user display device is a domestic user display device.

33. An article of manufacture comprising:
a machine-readable storage medium; and
executable program instructions embodied in the machine readable storage medium that when executed by a programmable system causes the system to perform the function of noise reduction in data regarding parameter values comprising the steps of:
- making a series of measurements of parameter values at times separated by predetermined time intervals;
- forming an array of measurements of parameter values comprising plural successive measurements of parameter values;
- performing a plurality n of successive wavelet transforms on the array of measurements of parameter values to produce an array of coefficients;
- comparing the values of the array of coefficients to a threshold value and, selectively changing the values of said coefficients based on their relationship to the threshold, to produce an array of filtered coefficients; and
- performing n successive inverse wavelet transforms on the array of filtered coefficients to produce an array of filtered measurements.

* * * * *